US012017008B2

(12) United States Patent
Prabhudesai et al.

(10) Patent No.: US 12,017,008 B2
(45) Date of Patent: *Jun. 25, 2024

(54) PRESSURE SAFETY DEVICE FOR BAG VALVE MASK

(71) Applicant: safeBVM Corp, Boston, MA (US)

(72) Inventors: Prathamesh P. Prabhudesai, Fremont, CA (US); Haris Shekhani, Chesterfield, MO (US); Iordache F. Tirdea, Pompano Beach, FL (US); Nadia Alam, Burbank, CA (US); Amrita Bhowmick, San Jose, CA (US); Ananya Gupta, Baltimore, MD (US); Liuyi Meng, Bloomington, IN (US)

(73) Assignee: safeBVM Corp, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/123,751

(22) Filed: Mar. 20, 2023

(65) Prior Publication Data

US 2023/0226306 A1 Jul. 20, 2023

Related U.S. Application Data

(63) Continuation of application No. 16/428,736, filed on May 31, 2019, now Pat. No. 11,628,269.
(Continued)

(51) Int. Cl.
*A61M 16/20* (2006.01)
*A61M 16/00* (2006.01)
*A62B 18/10* (2006.01)

(52) U.S. Cl.
CPC ...... *A61M 16/209* (2014.02); *A61M 16/0084* (2014.02); *A62B 18/10* (2013.01)

(58) Field of Classification Search
CPC .............. A61M 16/0084; A61M 16/20; A61M 16/208; A61M 16/209; F16K 15/148;
(Continued)

(56) References Cited

U.S. PATENT DOCUMENTS 2,593,315 A 4/1952 Kraft
2,777,464 A 1/1957 Mosely
(Continued)

FOREIGN PATENT DOCUMENTS

CN 107096106 A 8/2017
EP 1315534 A2 6/2003
(Continued)

OTHER PUBLICATIONS

Lecroy, S.C.A. Review of Neonatal & Infant Ventilation Methods. Journal of Emergency Medical Services Mar. 3, 2014 (Year: 2014).*
(Continued)

*Primary Examiner* — Kathryn E Ditmer
(74) *Attorney, Agent, or Firm* — Wilson Sonsini Goodrich & Rosati

(57) ABSTRACT

A pressure safety device is used with a bag valve mask (BVM) for preventing over-pressurization. The BVM includes a bag assembly having a bag connector for detachably mating to a mask connector on a patient mask. The pressure safety device has a housing with a bag port, a mask fitting, and a flow path from the bag port to the mask fitting. The bag port detachably connects to the bag connector on the BVM, and the mask fitting detachably connects to the mask connector on the BVM. The pressure safety device includes an automatic flow reduction valve located on the flow path in the housing and impedes flow when pressure on a bag connector side of the valve exceeds a maximum threshold value.

9 Claims, 6 Drawing Sheets

Related U.S. Application Data

(60) Provisional application No. 62/679,301, filed on Jun. 1, 2018.

(58) Field of Classification Search
CPC ..... F16K 17/025; F16K 17/28; G05D 7/0113; G05D 7/012; G05D 7/0133; G05D 7/014
See application file for complete search history.

(56) References Cited

U.S. PATENT DOCUMENTS

| | | | |
|---|---|---|---|
| 2,851,060 A | 9/1958 | Henry et al. | |
| 2,948,296 A | 8/1960 | Thorburn | |
| 3,326,242 A | 6/1967 | Parkison | |
| 3,419,031 A * | 12/1968 | Hesse | A61M 16/208 137/859 |
| 3,435,839 A | 4/1969 | Elder et al. | |
| 3,468,338 A | 9/1969 | Patterson et al. | |
| 4,071,025 A | 1/1978 | Kohnke | |
| 4,167,184 A | 9/1979 | Kohnke | |
| 4,239,038 A | 12/1980 | Holmes | |
| 4,325,366 A | 4/1982 | Tabor | |
| 4,344,459 A | 8/1982 | Nelson | |
| 4,374,521 A | 2/1983 | Nelson et al. | |
| 4,821,713 A | 4/1989 | Bauman | |
| 4,898,166 A | 2/1990 | Rose et al. | |
| 5,103,854 A | 4/1992 | Bailey et al. | |
| 5,301,667 A | 4/1994 | Mc et al. | |
| 5,409,042 A | 4/1995 | Kirchner | |
| 5,469,883 A | 11/1995 | Lee | |
| 5,537,998 A | 7/1996 | Bauman | |
| 5,557,049 A | 9/1996 | Ratner | |
| 5,632,298 A | 5/1997 | Artinian | |
| 5,722,394 A | 3/1998 | Loescher | |
| 5,727,546 A | 3/1998 | Clarke et al. | |
| 6,062,217 A | 5/2000 | Gray | |
| 6,062,247 A | 5/2000 | King, Sr. | |
| 6,604,523 B2 | 8/2003 | Lurie et al. | |
| 6,792,947 B1 * | 9/2004 | Bowden | A61M 16/0078 128/207.14 |
| 6,986,349 B2 | 1/2006 | Lurie | |
| 7,195,012 B2 | 3/2007 | Lurie | |
| 7,204,251 B2 | 4/2007 | Lurie | |
| 7,240,676 B2 | 7/2007 | Rutter | |
| 7,341,059 B2 | 3/2008 | Moody et al. | |
| 7,392,805 B2 | 7/2008 | Maguire | |
| 7,861,710 B2 | 1/2011 | Ingenito | |
| 8,167,002 B2 | 5/2012 | Kuhne et al. | |
| 8,348,227 B2 | 1/2013 | Zoller | |
| 10,098,809 B2 | 10/2018 | Ritter, III et al. | |
| 10,456,548 B2 | 10/2019 | Ackerman et al. | |
| 10,905,843 B2 | 2/2021 | Smith et al. | |
| 11,628,269 B2 | 4/2023 | Prabhudesai et al. | |
| 2001/0029950 A1 | 10/2001 | Haubeil | |
| 2003/0192547 A1 | 10/2003 | Lurie et al. | |
| 2004/0040559 A1 | 3/2004 | Moody et al. | |
| 2006/0191536 A1 | 8/2006 | Kroupa et al. | |
| 2007/0267019 A1 | 11/2007 | Lugtigheid | |
| 2008/0314386 A1 | 12/2008 | Myklebust et al. | |
| 2009/0260628 A1 | 10/2009 | Flynn, Sr. | |
| 2013/0025724 A1 | 1/2013 | Grebinoski et al. | |
| 2015/0000754 A1 | 1/2015 | Weingarten | |
| 2015/0096559 A1 | 4/2015 | Duval-Arnould et al. | |
| 2015/0238722 A1 | 8/2015 | Al-Ali | |
| 2016/0338619 A1 | 11/2016 | Roxhed et al. | |
| 2017/0198826 A1 | 7/2017 | Chen | |
| 2018/0021533 A1 | 1/2018 | Gausche-Hill et al. | |
| 2018/0147375 A1 | 5/2018 | Johnson et al. | |
| 2019/0168607 A1 | 6/2019 | Thebault | |
| 2019/0247595 A1 * | 8/2019 | Pohlmann | A61M 11/02 |

FOREIGN PATENT DOCUMENTS

| | | |
|---|---|---|
| FR | 1516113 A | 3/1968 |
| GB | 910065 A | 11/1962 |
| JP | H0868469 A | 3/1996 |
| JP | 2011500126 A | 1/2011 |
| KR | 101856869 B1 * | 6/2018 |
| WO | WO-0115761 A1 | 3/2001 |
| WO | WO-2009047763 A1 | 4/2009 |
| WO | WO-2010024680 A1 | 3/2010 |
| WO | WO-2012146369 A2 | 11/2012 |
| WO | WO-2016123562 A1 | 8/2016 |
| WO | WO-2019232491 A1 | 12/2019 |

OTHER PUBLICATIONS

Abella et al., Quality of cardiopulmonary resuscitation during in-hospital cardiac arrest. Jama. Jan. 19, 2005;293(3); pp. 305-310.

Ata Murat Kaynar, Respiratory Failure, Medscape, Updated Apr. 7, 2020, accessible online at "https://emedicine.medscape.com/article/167981-overview#a4".

Aufderheide, et al., Death by hyperventilation: a common and life-threatening problem during cardiopulmonary resuscitation. Critical Care Medicine. Sep. 2004;32(9 Suppl):S345-351.

Aufderheide et al., Hyperventilation-induced hypotension during cardiopulmonary resuscitation. Circulation. 2004; 109(16): 1960-1965, Originally published Apr. 5, 2004.

Bouvet et al., Real-time Detection of Gastric Insufflation Related to Facemask Pressure-controlled Ventilation Using Ultrasonography of the Antrum and Epigastric Auscultation in Nonparalyzed Patients A Prospective, Randomized, Double-blind Study, Anesthesiology, Feb. 2014;120(2):326-34.

Bucher et al., Bag Mask Ventilation (Bag Valve Mask, BVM). In: StatPearls. Treasure Island (FL) Feb. 7, 2022.

Cares. Cares Summary Report—Jan. 1, 2013 Through Dec. 31, 2016. 2016; Demographic and Survival Characteristics of OHCA, Apr. 18, 2017, Available online at: "https://mycares.net/sitepages/uploads/2017/2013-2016%20Non-Traumatic%20National%20Summary%20Report.pdf."

Clarke et al., Ventilatory characteristics in mechanically ventilated patients during manual hyperventilation for chest physiotherapy. Anaesthesia. Oct. 1999;54(10); pp. 936-940.

Coronary Heart Disease, National Heart, Lung, and Blood Institute, Last updated on Mar. 24, 2022, accessible at: >https://www.nhlbi.nih.gov/health/coronary-heart-disease.

Davidovic et al., Comparison of 1- versus 2-person bag-valve-mask techniques for manikin ventilation of infants and children. Annals of emergency medicine, Jul. 2005; 46(1); pp. 37-42.

EP19810067.9 Extended European Search Report dated Feb. 10, 2022.

Gammon et al., Pulmonary barotrauma in mechanical ventilation. Patterns and risk factors, Chest, Aug. 1992; 102(2):568-72.

International Search Report and Written Opinion for PCT/US2019/035075 dated Aug. 22, 2019.

Karlsson et al., Central and regional blood flow during hyperventilation. An experimental study in the pig. Acta Anaesthesiol Scand. Feb. 1994;38(2); pp. 180-186.

Keller et al., Cardiac arrest: the changing incidence of ventricular fibrillation, Current Treatment Options in Cardiovascular Medicine, Jul. 2015; 17(7):392, Published: May 16, 2015.

Kern et al., Metronome improves compression and ventilation rates during CPR on a manikin in a randomized trial, Resuscitation, Feb. 2010;81(2); pp. 206-210.

Khoury et al., Evaluation of Bag-Valve-Mask Ventilation in Manikin Studies: What Are the Current Limitations? Biomed Research International. 2016; Article ID 4521767; Published May 16, 2016.

Khoury et al., Performance of manual ventilation: how to define its efficiency in bench studies? A review of the literature. Anaesthesia. Aug. 2015;70(8); pp. 985-992, Epub May 21, 2015.

Lecroy, S.C.A. Review of Neonatal & Infant Ventilation Methods. Journal of Emergency Medical Services Mar. 3, 2014.

Lindström et al., End-tidal carbon dioxide monitoring during bag valve ventilation: the use of a new portable device. Scandinavian Journal of Trauma Resuscitation Emergency Medicine, 2010;18:49, Published: Sep. 14, 2010.

(56) References Cited

OTHER PUBLICATIONS

Losert et al., Quality of cardiopulmonary resuscitation among highly trained staff in an emergency department setting. Arch Intern Med., Nov. 27, 2006; 166(21); pp. 2375-2380.
Manual Resuscitators Market Analysis by Type (Self-inflating, Flow-inflating) By End-use (Hospitals, Outside Hospital), And Segment Forecasts to 2024, Grand View Research, Aug. 2016, Accessed via the Internet Wayback Machine at "https://web.archive.org/web/20170627032122/https://www.grandviewresearch.com/industry-analysis/manual-resuscitators-market".
McInnes et al., The first quantitative report of ventilation rate during in-hospital resuscitation of older children and adolescents. Resuscitation. Aug. 2011;82(8); pp. 1025-1029, Epub Mar. 29, 2011.
MEDUMAT Easy CPR—The Guiding Emergency Ventilator, Weinmann Medical Technology, 2015; accessible at "title="Link: http://medak.dk/MEDUMAT_Easy_CPR_83535-EN.pdf>> http://medak.dk/MEDUMAT_Easy_CPR_83535-EN.pdf.
Milander et al., Chest compression and ventilation rates during cardiopulmonary resuscitation: the effects of audible tone guidance. Academic emergency medicine : official journal of the Society for Academic Emergency Medicine. Aug. 1995; 2(8); pp. 708-713.
Mozaffarian et al., Executive Summary: Heart Disease and Stroke Statistics—2016 Update: A Report From the American Heart Association, Circulation, Jan. 26, 2016;133(4); pp. 447-454.
Neumar et al., Part 8: Adult Advanced Cardiovascular Life Support2010 American Heart Association Guidelines for Cardiopulmonary Resuscitation and Emergency Cardiovascular Care, Circulation, Nov. 2, 2010; 122 (18 Suppl 3):S729-67.
Nichol et al., Treatment for out-of-hospital cardiac arrest: is the glass half empty or half full? Circulation. 2014; 130(21): 1844-1846, Originally published Nov. 15, 2014.
Niebauer et al., Hyperventilation in pediatric resuscitation: performance in simulated pediatric medical emergencies. Pediatrics. Nov. 2011;128(5):e 1195-1200, Epub Oct. 3, 2011.
O'Neill, Do we hyperventilate cardiac arrest patients? Resuscitation, Apr. 2007.;73(1):82-85.
Prekker et al., The epidemiology and outcome of prehospital respiratory distress, Academic Emergency Medicine, May 2014;21(5); pp. 543-550.
Qian et al., Determination of the optimal inspiratory pressure providing adequate ventilation while minimizing gastric insufflation using real-time ultrasonography in Chinese children: a prospective, randomized, double-blind study, BMC Anesthesiology, vol. 17, No. 1; Article No. 126, Published: Sep. 11, 2017.
Robinson et al., Evaluation of the self-inflating bag-valve-mask and non-rebreather mask as preoxygenation devices in volunteers, BMJ Open, Oct. 26, 2012;2(5):e001785.
Stefan et al., Epidemiology and outcomes of acute respiratory failure in the United States, 2001 to 2009: a national survey. Journal of Hospital Medicine, Feb. 2013;8(2); pp. 76-82.
Stiell et al., Advanced life support for out-of-hospital respiratory distress. The New England journal of medicine. 2007;356(21):2156-2164.
Sunde, et al. Airway management by physician-staffed Helicopter Emergency Medical Services—a prospective, multicentre, observational study of 2,327 patients. Scandinavian Journal of Trauma, Resuscitation and Emergency Medicine, 23, 57; Published: Aug. 7, 2015.
U.S. Appl. No. 16/428,736 Notice of Allowance dated Dec. 21, 2022.
U.S. Appl. No. 16/428,736 Notice of Allowance dated Sep. 9, 2022.
U.S. Appl. No. 16/428,736 Office Action dated Dec. 24, 2021.
Vicente et al., Portable automated bag-valve mask with android technology, International Journal of Advanced Technology and Engineering Exploration, vol. 3(16), Published Mar. 24, 2016.
Von Goedecke A, et al. Mechanical versus manual ventilation via a face mask during the induction of anesthesia: a prospective, randomized, crossover study. Anesth Analg. 2004;98(1); pp. 260-263.
Von Goedecke A et al., Ventilation of an unprotected airway; Evaluation of a new peak-inspiratory-flow and airway-pressure-limiting bag-valve-mask, Der Anaesthesist; Jun. 2006;55(6); pp. 629-634 (Abstract Only in English).
Wahlen et al., Gastric insufflation pressure, air leakage and respiratory mechanics in the use of the laryngeal mask airway (LMA) in children, Paediatric Anaesthesia, Apr. 2004; 14(4); pp. 313-317.
Weiler et al., Assessment of pulmonary mechanics and gastric inflation pressure during mask ventilation. Prehospital Disaster Medicine, Apr.-Jun. 1995; 10(2): 101-105.
Weiler et al., Respiratory mechanics, gastric insufflation pressure, and air leakage of the laryngeal mask airway, Anesthesia & Analgesia: May 1997—vol. 84—Issue 5; pp. 1025-1028.

\* cited by examiner

PRESSURE SAFETY DEVICE FOR BAG VALVE MASK

CROSS-REFERENCE

This application is a continuation of U.S. patent application Ser. No. 16/428,736, filed May 31, 2019, which claims the benefit of U.S. Provisional Application No. 62/679,301, filed Jun. 1, 2018, which application is incorporated herein by reference.

BACKGROUND OF THE INVENTION

1. Field of the Invention

The present invention relates generally to medical devices and methods. More particularly, the present invention relates to the field of breathing gas delivery using manual resuscitators.

Bag valve mask resuscitators (BVM's) have long used to manually ventilate patients who cannot breathe on their own, such as those in cardiac arrest, suffering respiratory distress, under anesthesia, and the like. Conventional BVM's have a compression bag that is manually compressed by a user to pressurize and deliver a breathing gas to a patient through a breathing mask held over the patient's mouth and nose.

Poor manual technique using a BVM can be problematic. In particular, over-pressurization of the compression bag and increase both breathing gas pressure and flow rate over optimum levels, and in the worst cases can potentially harm the patient and in some cases safe levels, for example causing air entry into the stomach. While some solutions have been proposed, such as placing pressure relief valves in the flow path between the compression bag and the breathing mask, the resulting venting is not always effective and there is no tactile or other feedback to the user to alert them that they need to lessen the pressure that they are applying.

It is thus an object of the present invention to provide alternative and improved apparatus and methods for limiting over-pressurization when using a BVM. In particular, it is an object of the present invention to limit the delivery of over-pressurized BVM breathing gases without venting. It is a further object of the present invention to provide tactile or other feedback to a user when such over-pressurization occurs. At least some of the objects will be met by the inventions described and claimed herein.

2. Background Art

U.S. Pat. No. 5,557,049 discloses a disposable manometer as an accessory to the BVM to indicate pressure of gas being delivered to the patient. U.S. Pat. No. 5,722,394 shows a BVM having a high pressure exhaust valve. U.S. Pat. No. 5,537,998 discloses a spring-loaded piston which sense and exhausts excess air pressure. U.S. Pat. No. 4,898,166 discloses a resuscitation bag control apparatus, U.S. Pat. No. 6,792,947 discloses a BVM having flow control. U.S. Pat. No. 2015/0096559A1 discloses feedback sensors for a BVM.

SUMMARY OF THE INVENTION

The present invention is useful in optimizing airflow to patients during manual ventilation with a bag valve mask (BVM) resuscitator to maintain adequate ventilation and lung perfusion while minimizing air entry into the stomach. In particular, the present invention controls inspiratory pressure to the patient by blocking airflow from the compression bag of the BVM when an optimum out flow pressure is exceeded. In addition to protecting the patient, stiffening of the bag caused by back pressure provides "tactile feedback" to the user as a teaching or reinforcement toll for proper manual ventilation technique.

The present invention thus enhances the safety while performing manual ventilation using a BVM resuscitator and can minimize complications in concurrent procedures, such as gastric insufflation, aspiration, aspiration pneumonia, Acute Respiratory Distress Syndrome (ARDS), cardiopulmonary compromise. The present invention can also reduce human errors and variability, improving quality of patient care, and reduce the cost of care delivery to the health system.

The invention may be used with any positive pressure air delivery device, impedance threshold accessory device, air filter and/or resuscitation outlet device, such as a mask, endotracheal tube, laryngeal mask airway, oral mask and the like. The invention may also be used for air delivery to any entity other than a patient like a lung simulation system, animal, cadaver, training equipment and the like.

In a first aspect, the present invention provides a pressure safety device for use with a bag valve mask (BVM). The BVM typically includes a bag assembly having a bag connector for detachably mating to a mask connector on a patient mask. The bag assembly will also typically have at least a compression bag which allows a user to manually compress the compression bag to deliver a volume or bolus of air or other breathing gas to a patient via the mask. The BVM may include various other components typical of conventional manual gas resuscitators.

The pressure safety device of the present invention will include a housing and an automatic flow reduction valve. The housing will typically have a bag port, a mask fitting, and an interior with passageways configured to define a flow path from the bag port to the mask fitting. The bag port will usually be configured to detachably connect to the bag connector on the BVM, and the mask fitting will typically be configured to detachably connect to the mask connector on the BVM. The automatic flow reduction valve is located on or along the flow path in the housing and will be configured to impede flow when a pressure or flow rate of a breathing gas through the automatic flow reduction valve or a pressure on a bag connector side of the automatic flow reduction valve exceeds a maximum threshold value.

In specific instances, the automatic flow reduction valve may be configured to impede flow when a maximum threshold pressure value comprises a pressure in the range 5 mmHg to 20 mmHg, usually in a range from 9 mmHg to 15 mmHg. Alternatively or additionally, the automatic flow reduction valve may be configured to impede flow when a maximum threshold flow value comprises a peak flow rate in the range 30 l/min to 70 l/min, typically from 35 l/min to 50 l/min.

The automatic flow reduction valves of the present invention will typically have any one of a number of conventional mechanical designs such as umbrella valves, spring-piston valves, and the like. Alternatively, the automatic flow reduction valves of the present invention could incorporate electronic components includes, pressure sensors, flow sensors, microprocessor controllers, powered valves, and the in order to block or inhibit flow through the BVM in accordance with the principles of the present invention described herein.

The automatic flow reduction valve may in some instances be configured to fully block flow and/or to partially block flow in other instances. by "partially blocked flow," it is meant that the flow rate will be reduced by at least 50% of an unrestricted value, typically at least 60% of the unrestricted value, often at least 75% of the unrestricted value, and many times at least 90% or more of the unrestricted value. In other instances, the automatic flow reduction valve maybe adjustable so that it can be set to fully block flow or to partially block flow depending on the desired use. For example, the spring of a spring-piston type valve could have a variable set point or variable loading adjustment to allow the pressure or flow rate set point at which the valve closes to be changed. It will be appreciated that when the automatic flow reduction valve does not fully block flow, there will be a residual bypass flow path remaining for breathing gas to be delivered to the patient at a reduced pressure and/or flow rate.

The pressure safety device of the present invention may further comprise a one-way valve placed in or along the flow path from the bag port to the mask fitting, where the one-way valve will be oriented to block or divert an exhalation flow which enters the housing from the BVM mask through the mask fitting. Typically, the housing will be configured to have fenestrations or other openings oriented to release the diverted or blocked exhalation flow from the one-way valve to an exterior of the housing. Changes in a flow resistance provided by the fenestration can be used to build or otherwise control pressure inside lung (PEEP).

In a second aspect, the present invention provides methods for modifying, typically reversibly, a bag valve mask (BVM) which includes a bag assembly and a bag connector as described above. The methods for modifying the BVM according the present invention comprise providing a pressure safety device (PSD) having a bag port in a mask fitting, and connecting the bag port and the mask fitting of the PSD to the bag connector and the mask connector of the BVM, respectively. The PSD will be configured to impede breathing gas flow from the BVM to patient when a pressure or flow rate of the breathing gas entering the bag port of PSD exceeds a maximum threshold value.

Specific aspects of the PSD and its use in connection with the BVM have been described previously in connection with the construction of the PSD.

In a third aspect, the present invention provides a bag valve mask (BVM) assembly which includes a manifold, a compression bag attached to deliver a breathing gas to the manifold, and a breathing mask attached to receive the breathing gas from the manifold. In accordance with the principles of the present invention, an automatic flow reduction valve is located on flow path in the manifold between the compression valve and the breathing mask. The automatic flow reduction valve is configured to impede flow a flow rate or a pressure on the compression bag side of the automatic flow reduction valve exceeds a maximum threshold value.

As with the previous devices and methods described above, the automatic flow reduction valve may be configured to impede flow when a maximum threshold pressure value comprises a pressure in the range 5 mmHg to 20 mmHg, usually in a range from 9 mmHg to 15 mmHg. Alternatively or additionally, the automatic flow reduction valve may be configured to impede flow when a maximum threshold flow value comprises a peak flow rate in the range 30 l/min to 70 l/min, typically from 35 l/min to 50 l/min.

Other features and specifications of the automatic flow reduction valve of BVM assembly may be as described previously with respect to the PSD and to method for modifying the BVM.

In a fourth aspect of the present invention, a method for delivering a breathing gas to a patient comprises placing a breathing mask over the patient's mouth and nose. A compression bag is then compressed to deliver the breathing gas to the breathing mask and to the patient. A flow of breathing gas delivered to the breathing mask is impeded if a pressure or flow rate from the breathing gas bag exceeds maximum value.

In specific instances of these methods, impeding the flow of the breathing gas to the mask comprises placing an automatic flow reduction valve in a flow path between the compression bag and the breathing mask. The automatic flow reduction valve will be configured to impede the breathing gas flow when a flow rate or pressure from the compression bag exceeds a maximum threshold value.

The automatic flow reduction valve may be incorporated directly into the structure of the BVM or, alternatively, may be provided as a separate PSD as described above. Specific characteristics of the automatic flow reduction valve may be generally the same as previously described in the devices and methods of the present set forth above.

Certain embodiments of the present invention are particularly advantageous in that the PSD can be removed from the BVM when treating certain conditions where there is an obstructive or restrictive condition requiring the use of high pressure to deliver adequate volumes during manual ventilation. In other cases, however, it will be possible to have the PSD incorporated as an integrated component in the manifold or other structure of the BVM with an override mechanism to allow high pressure ventilation ungoverned by the PSD component.

The PSD of the present invention is configured to be hand-held, light weight, portable, durable, and cost-efficient to meet the criteria for adoption in an Emergency Medical Services (EMS) space. During ventilation, as the device forms a continuous air column with the lung, the pressure threshold for the flow blocking valve is relative to the patient's intrathoracic pressure, resulting in personalization of the threshold to optimize airflow to the lung while preventing gastric insufflation.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
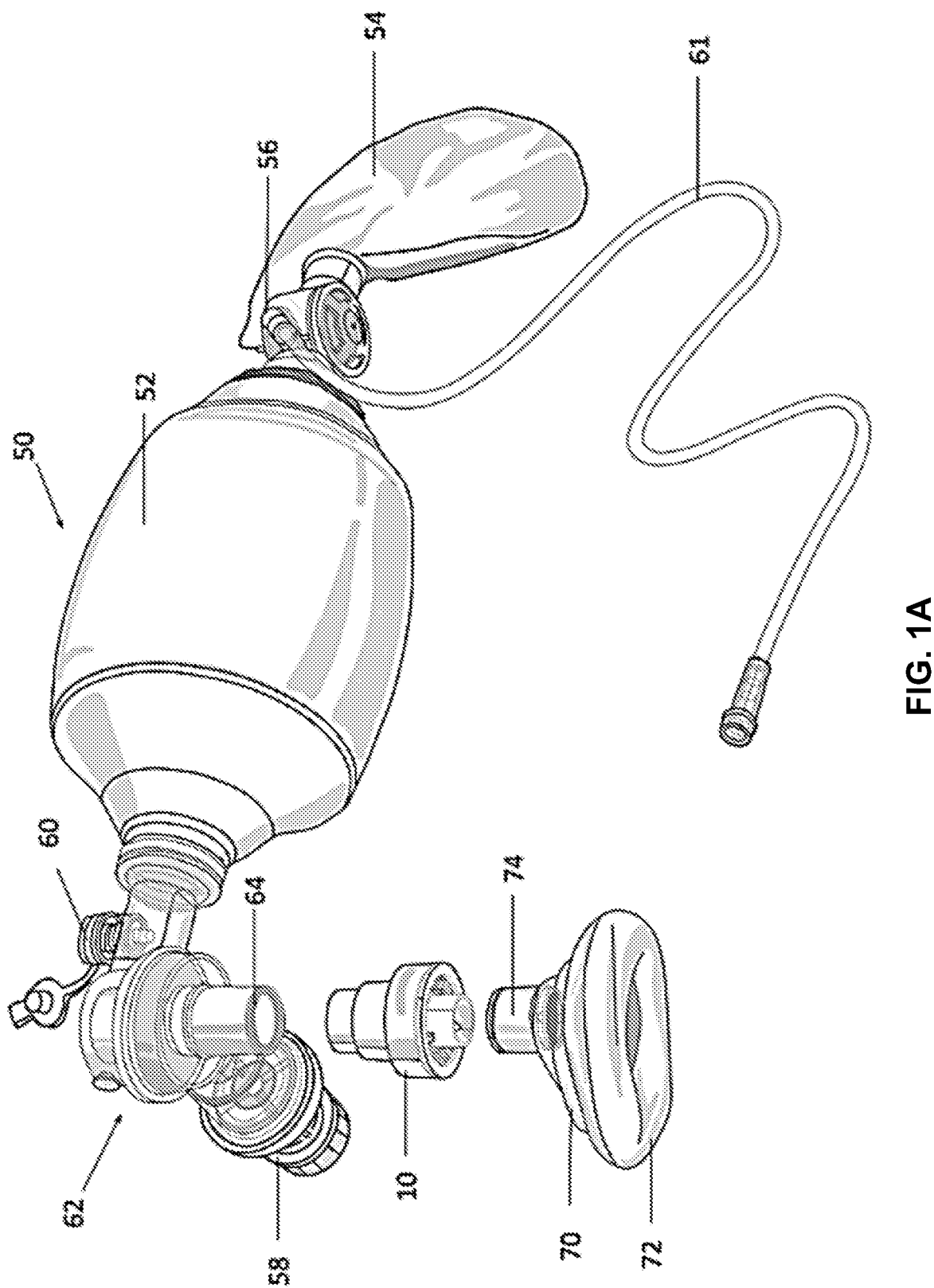
FIGS. 1A and 1B illustrate a conventional bag valve mask (BVM) apparatus having a pressure safety device of the present invention incorporated therein.
Figure 1B:
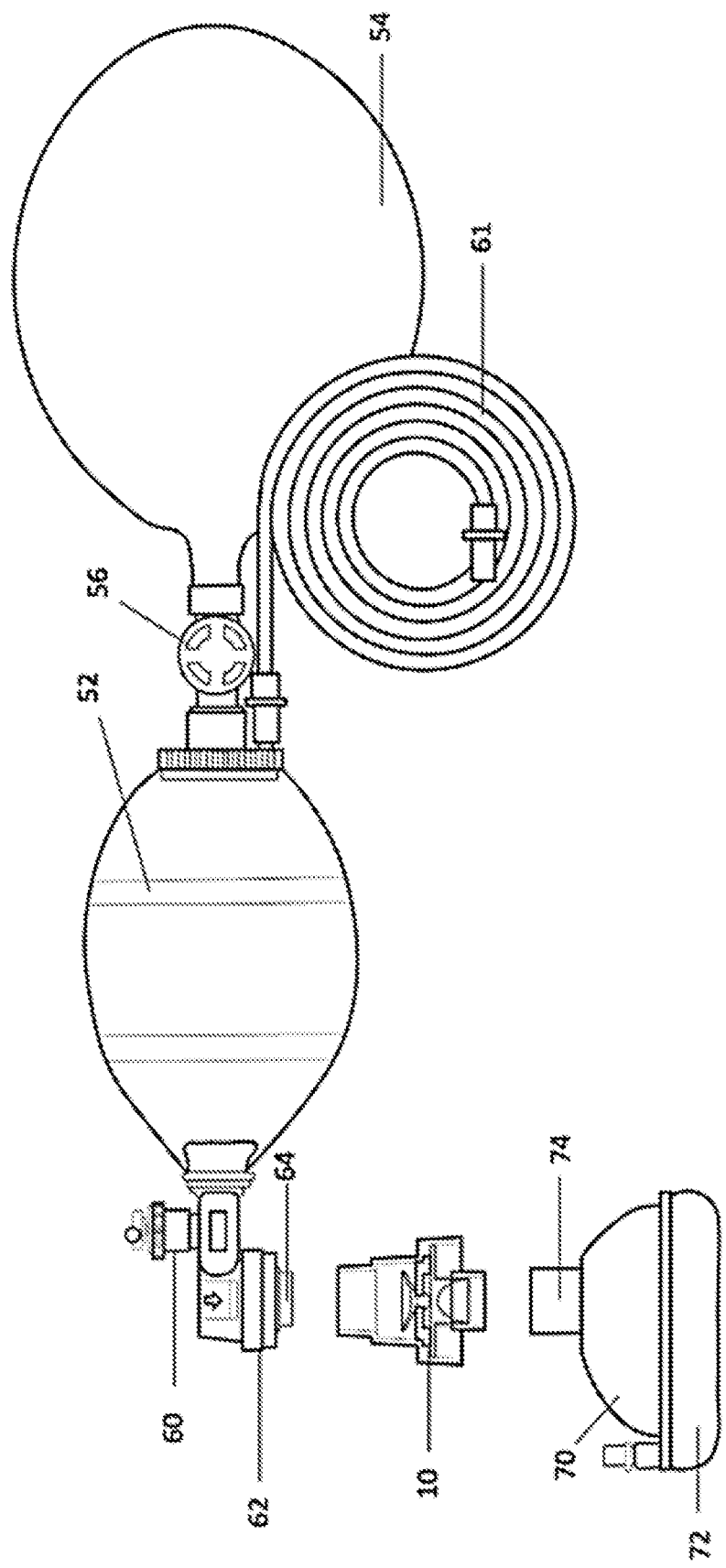

FIGS. 1A and 1B show a pressure safety device (PSD) 10 constructed in accordance with the principles of the present invention in its intended position within a standard bag valve mask (BVM) assembly 50. The BVM 50 includes a compression bag 52, a reservoir bag 54 connected to the compression bag by a reservoir valve 56, a positive end expiratory pressure (PEEP) valve 58, and a pop-off valve 60. The compression bag 52, PEEP valve 58 and pop-off valve 60 are all connected to a manifold 62 having a connector port 64 for removably receiving a breathing mask 70. The breathing mask 70 typically has an air cushion 72 on one surface for placing over a patient's mouth and nose when in use and a connector fitting 74 for detachably mating to the connector port 64 of the manifold 62. Commonly, the connector port 64 on the manifold 62 will be a male connector and the connector fitting 74 on the breathing mask 70 will be a female fitting, but the present invention can be adapted to work with any pair of detachable connectors, including screw connectors, bayonet connectors, latched connectors, and the like.

As described thus far, the BVM 50 is entirely conventional, and will be ready for use once the connector port 64 of the manifold 62 has been inserted directly into the connector fitting 74 of the breathing mask 70. Usually, at least the breathing mask 70 will be disposable and kept in a sterile pack before use.

In exemplary embodiments, the PSD of the present invention is intended for use with a standard BVM such as BVM 50 just described. While the PSD can be constructed in various ways, the main components will include an "automatic flow reduction valve," such as a blocking valve, to prevent excess flow and/or pressure from being delivered to the breathing mast 70. The PSD 10 may also include a one-way valve that prevents patient exhalation from returning to the BVM, typically redirecting the exhalation flow outwardly through openings in the PSD.

The "automatic flow reduction valve" or "AFRD" of the present invention can take any one of a variety of forms. While typically being a dome-shaped flap valve or a spring-loaded shut-off valve as described below, the AFRD can be any type of pressure-response or flow-responsive valve which is capable of being located along an inhalation flow path to the patient and reducing or stopping a flow of breathing gas from the compression bag to the patient whenever the flow or pressure exceeds a maximum threshold value.

Referring again to FIGS. 1A and 1B, a conventional bag valve mask assembly (BVM) comprises a compression bag 52, a reservoir bag 54, reservoir valve 56, a PEEP valve 58, a pop-off valve 60, and an oxygen tube 61. The compression bag 52, pop-off valve 60 and PEEP valve 58 are all connected to a manifold 62 having a connector port 64 on a lower end thereof. In particular, the compression bag 52 is constructed to deliver breathing gas from the oxygen tube 61 through the manifold 62 and out the connector port 64.

In a conventional BVM, a breathing mask 70 having an air cushion 72 on its lower surface and a connector fitting 74 on an upper surface will be connected directly to the manifold 62. In particular, the connector port 64 is typically a male fitting which fits in a female connector fitting 74 so that breathing gas from the manifold flows directly into the breathing mask 70. The BVM may then be used by placing the air cushion 72 over a patient's nose and mouth and manually squeezing the compression bag 52 to deliver breathing gas to the patient.

In accordance with the present invention, however, a pressure safety device (PSD) can as provided for insertion between the connector port 64 of the BVM 50 and the connector fitting 74 of the breathing mask 70. As described in more detail below, the pressure safety device may take a variety of specific forms, but will be designed and configured to limit over pressurization and/or overflow of breathing gas from the compression bag 52 to the patient.

Figure 2:
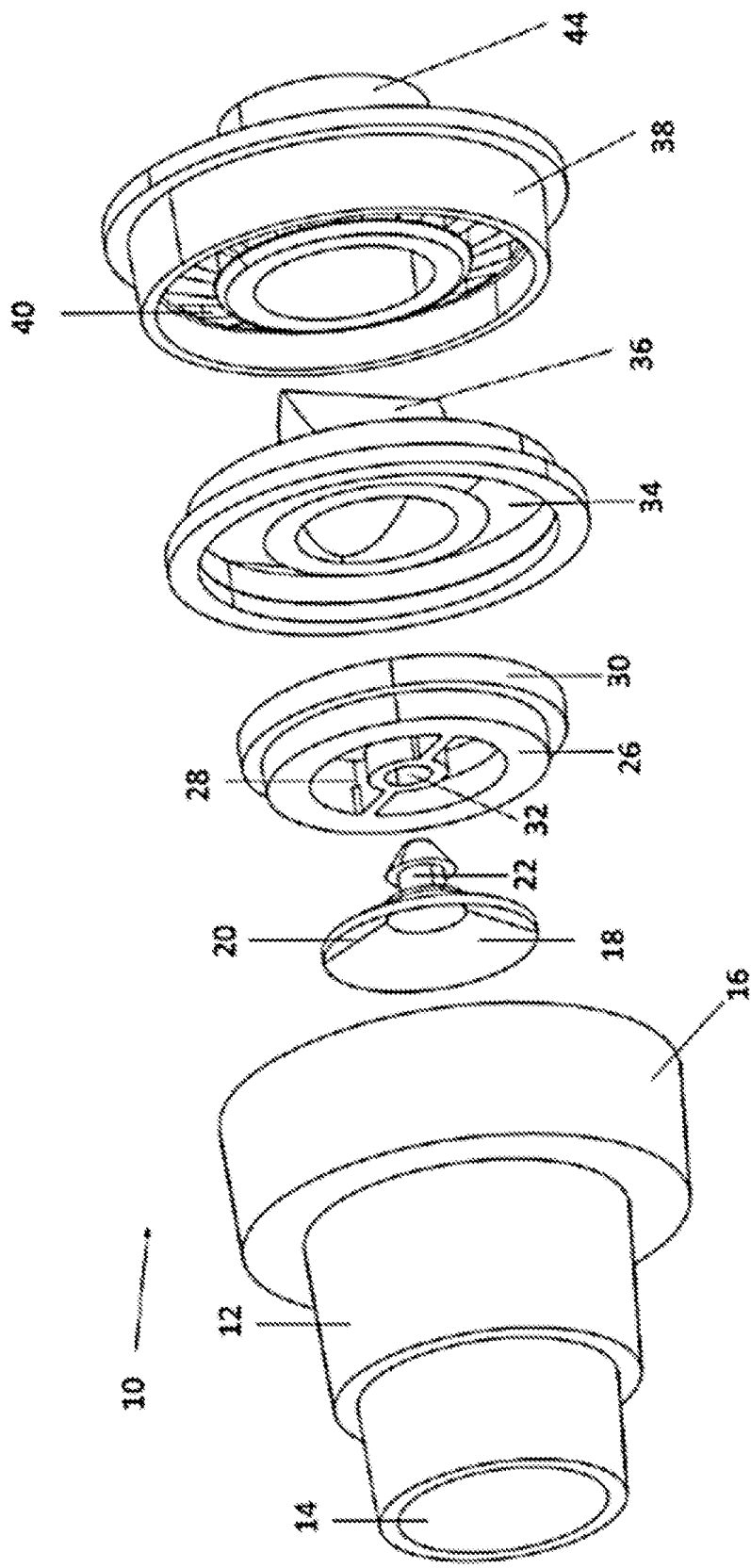
FIG. 2 is an exploded view of a first embodiment of a pressure safety device of the present invention having an umbrella valve as the automatic flow reduction valve.

In the first embodiment, as shown in FIG. 2, a PSD 10 comprises a housing 12 having a bag port 14 and base 16. An umbrella valve 18 is provided as an automatic flow reduction valve and includes a deformable seal 20, typically in the form of a conical seal capable of everting to block or reduce flow as described below.

The umbrella valve 18 is mounted on a support plate 26 having a plurality of flow openings or passages 28 formed therethrough. A dagger-type anchor 22 is mounted in a hole 32 in the support plate 26 to properly position the deformable seal 20 so that a conical periphery of the seal is deflected upwardly away from the support plate 26 when the seal is in an unstressed, undeformed configuration. The conical periphery of the seal 20, however, will close downwardly over the flow openings or passages 28 when excess pressure or breathing gas flow occurs on an upstream side of the deformable seal (the side closer to the bag port).

The support plate 26 is mounted in a one-way valve fitting 34 having a duckbill valve 36 aligned to receive breathing gas outflow from the flow openings 28 in the support plate 26. The duckbill valve is oriented so that breathing gas flowing from the bag port 14 which flows through the open umbrella valve 18 will open the duckbill and freely flow therethrough. Exhalation flow from the patient, however, will close the duckbill valve 36 and prevent patient exhalation of being transmitted back to the BVM.

The PSD 10 further comprises a bottom plate 38 having a polarity of fenestrations 40 formed in in an annular ring about its periphery. The fenestrations 40 may be any sort of passage which allows a an exhalation gas stream which is blocked by the duckbill valve 36 to flow downwardly and outwardly away from the housing 12 through the fenestrations. A mask fitting 44 is formed at the bottom of the bottom plate to provide for connection to the breathing mask 70, as illustrated in FIGS. 1A and 1B.

Figure 3A:
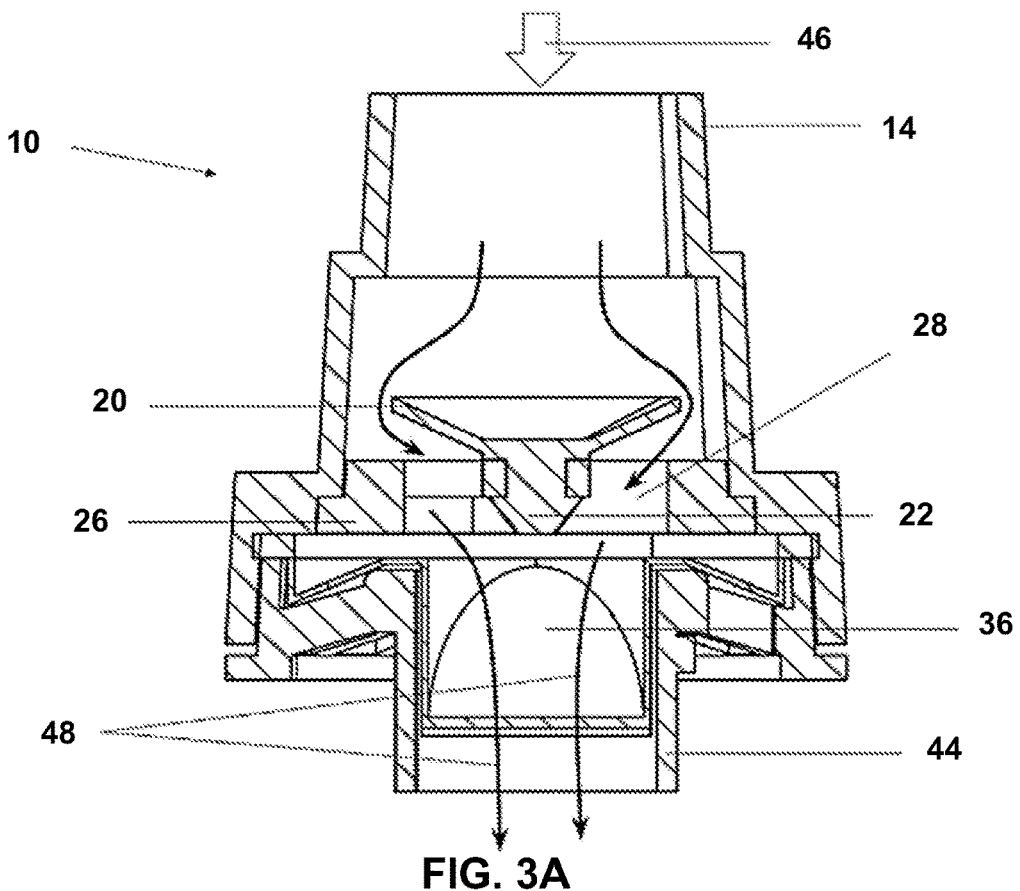
FIGS. 3A and 3B are cross-sectional views of the pressure safety device of FIG. 2 with the umbrella valve shown in an open configuration in FIG. 3A and in a closed configuration in FIG. 3B.
Figure 3B:
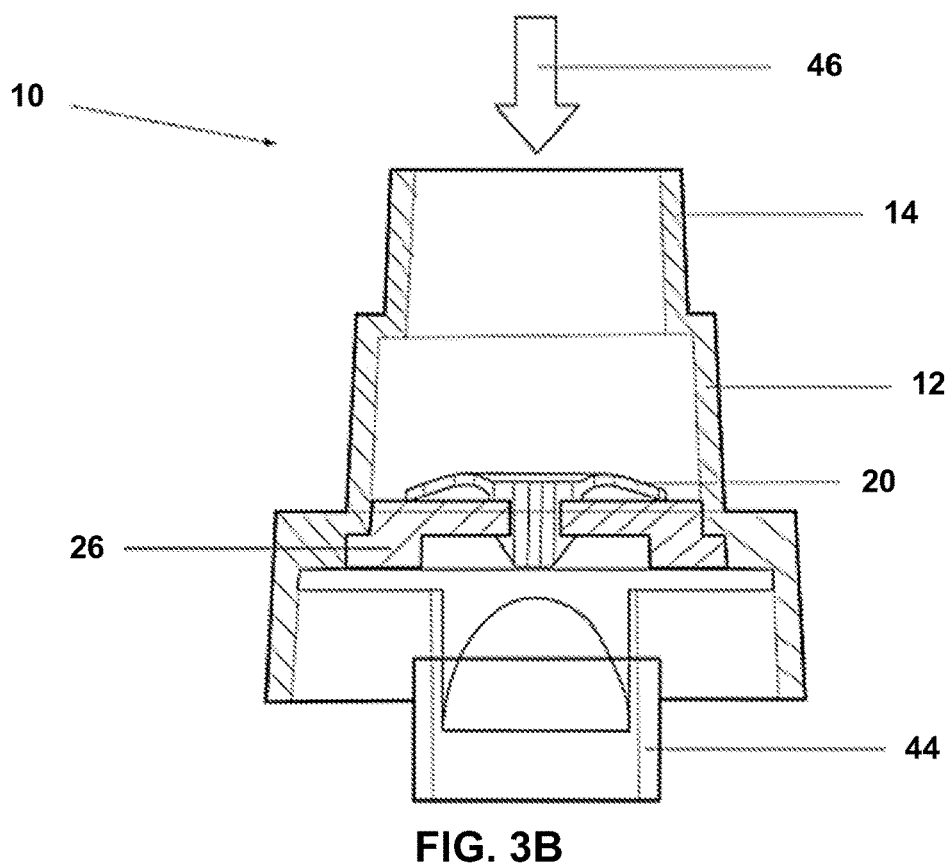

Referring now to FIGS. 3A and 3B, the PSD 10 is shown with the conical periphery of the deformable seal 20 of the umbrella valve 18 in its open, upwardly disposed configuration. In this configuration, air flow 46 entering the bag port 14 travels beneath the deformable seal 20 and through the flow openings 28 in the support plate 26, as shown by flow path arrows 48.

In contrast, when the entering air flow 46 exceeds a maximum threshold value for flow rate and/or pressure above the deformable seal 20, as shown in FIG. 3B, the seal will depressed downwardly to close over the flow openings 28 and stop (or reduce) the delivery of breathing gas to the patient. Partial blockage could be achieved, for example, by perforating the deformable seal 20 to permit a residual bypass flow even when the seal is closed.

Figure 4:
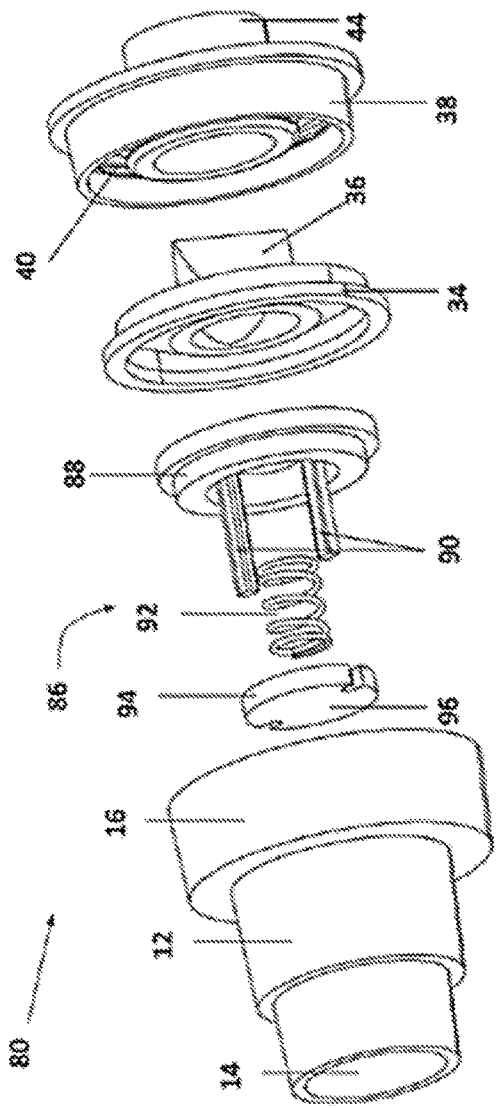
FIG. 4 is an exploded view of an alternative embodiment of a pressure safety device constructed in accordance with the principles of the present invention and having a spring-loaded valve as the automatic flow reduction valve.
Figure 5:
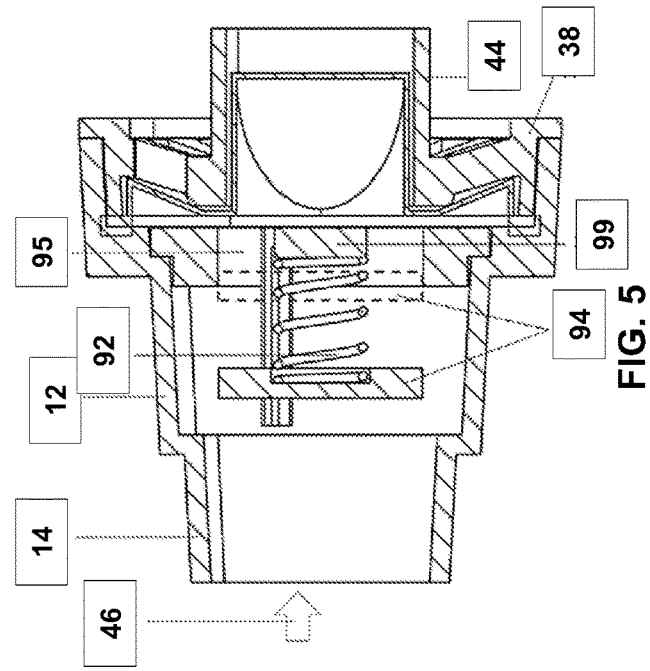
FIG. 5 is cross-sectional view of the pressure safety device of FIG. 4 is showing a seal plate of the spring-loaded valve in an open configuration (full line) and a closed configuration (broken line).
Figure 6:
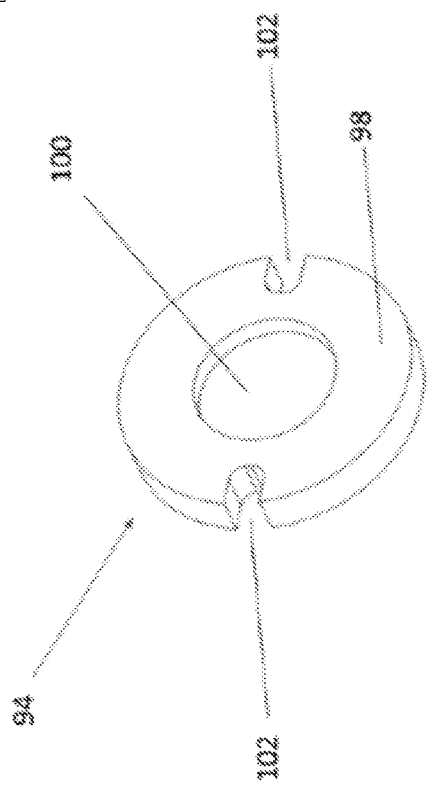
FIG. 6 is a detailed view of the seal plate of the spring-loaded valve.

Referring now to FIGS. 4 thru 6, a second PSD embodiment 80 having a spring-loaded valve as the automatic flow reduction valve is illustrated. The housing 14, one-way valve 34, and bottom plate 38 of PSD 80 may all be identical to those described previously with respect to PSD 10. The automatic flow relief valve, however, will be a spring-loaded valve 86 having a support plate 88 with guide posts 90. A seal plate 94 having guide slots 102 is slidably received over the guide posts 90, and a spring 92 is place between the guide posts and has a lower end received on a support surface 99 of the support plate 88 and an upper end received in a recess 100 formed in a lower surface of the seal plate 94.

As best seen in FIG. 5, the spring 92 while in an unconstrained configuration holds the seal plate 94 well above the flow openings 95 in the support plate 88 so that a breathing gas may flow from the compression bag 52 may flow in through the bag port 14 and out through the mask fitting 44. When the pressure and/or flow rate of the incoming the breathing gas flow 46 exceeds the maximum threshold value, however, the seal plate 94 will be moved downwardly to the position shown in broken line in FIG. 5 to close the openings 95 and inhibit or fully block the flow of breathing gas.

Figure 7A:
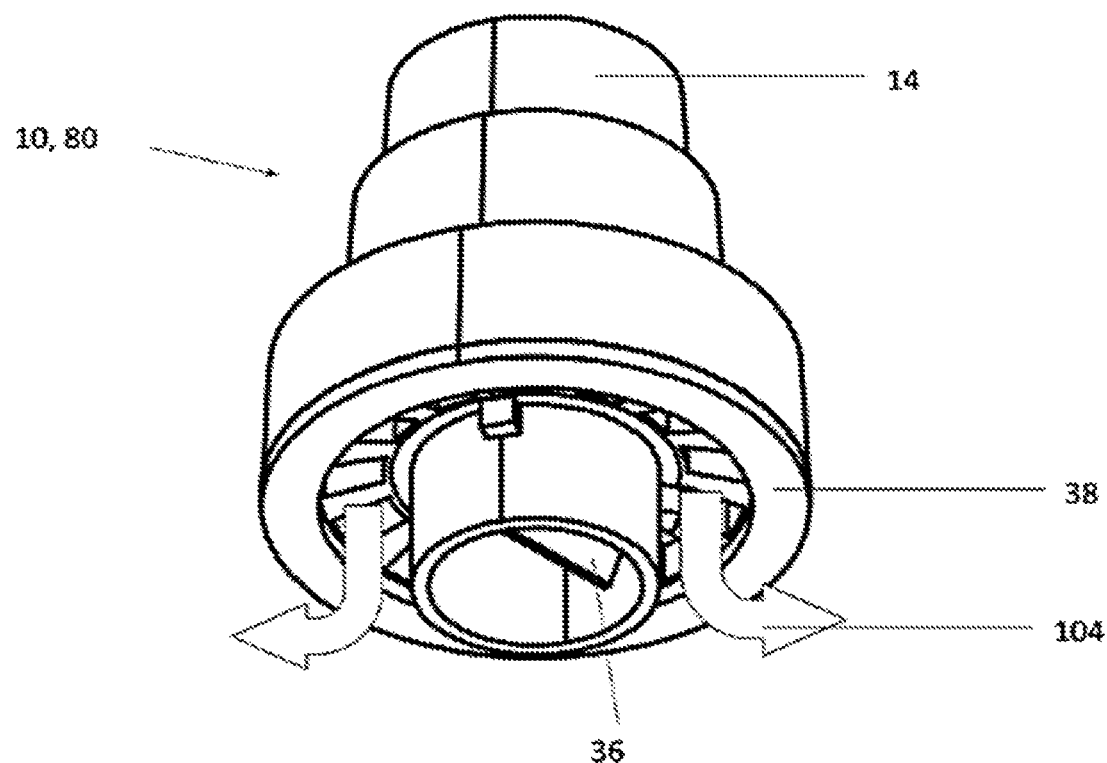
FIGS. 7A and 7B illustrate fenestrations in a housing of the pressure safety device for the release of exhalation gases from the patient blocked by a one-way valve in the pressure safety device.
Figure 7B:
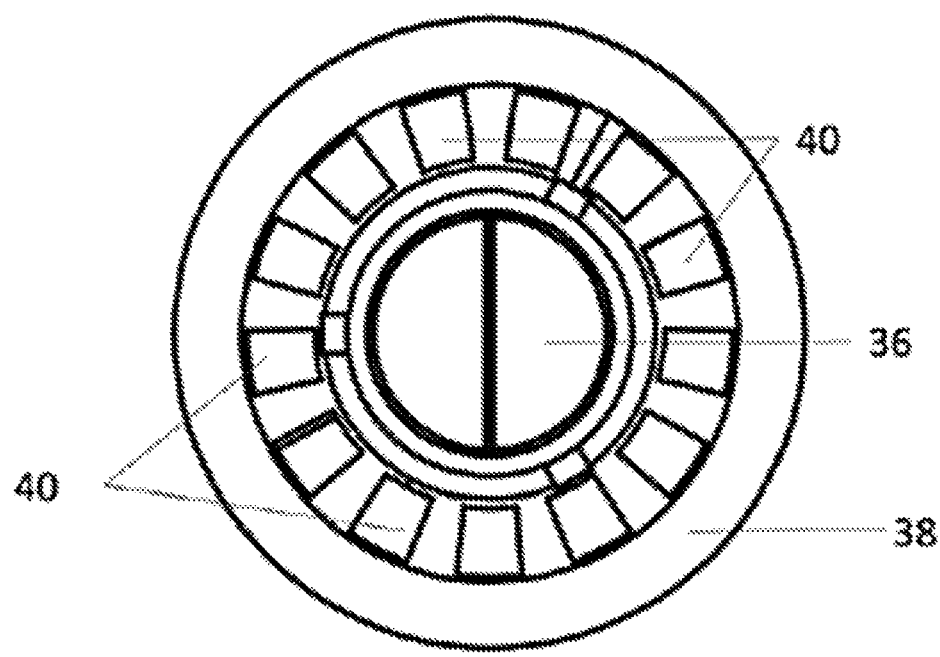

As shown in FIGS. 7A and 7B, when the patient exhales, the pressure of the exhalation gases which attempts to flow in reverse through the connector port 64 will close the duckbill valve 36, causing the exhalation gases to flow radially outwardly and then downwardly through the fenestrations 40 formed in the bottom plate 38, as indicated by arrows 104 in FIG. 7A. In this way, exhalation gases will not be forced back into BVM, preventing contamination. The fenestrations 40 can be altered to bring about changes in the pressure inside the lung during and after exhalation, referred to as Positive End Expiratory Pressure or PEEP. An increase in the fenestration 30 size and/or number, will decrease resistance and reduce the PEEP. Similarly, a decrease in the fenestration 40 size and/or number, will increase resistance against expiration and increase the PEEP. High PEEP helps to maintain the airway open during conditions like chronic obstructive pulmonary disease (COPD) where the airway has a tendency to collapse after expiration.

A standard BVM incorporating the PSD of the present invention may be used as follows. With one hand, a user holds the mask 70 placing the air cushions 72 over the nose and the mouth of the patient to obtain a tight seal and prevent leakage of air. The user's other hand continuously squeezes and releases the compression bag 52 of the BVM 50 to pump air from the reservoir bag 54 through the reservoir valve 56 to the mask 70 into the patient's lung. Should the flow or pressure delivered by the compression bag exceed the maximum threshold limits defined elsewhere herein, the AFRD18 or 86 of the PSD 10 will reduce or stop breathing gas flow to the patient to reduce the risk of injury.

The devices and methods of the present invention can be used in combination with other rusticator features, such as a cadence indicator as described in U.S. Pat. No. 10,098,809 and U.S. Pat. Publ. No 2003/0192547, the complete disclosures of which are herein incorporated by reference. The devices and methods of the present invention can also be used in combination with devices for managing intrathoracic pressure, such as an impedance threshold device (ITD) as described in in U.S. Pat. Nos. 6,604,523; 6,986,349; 7,195,012; and 7,204,251, the complete disclosures of which are herein incorporated by reference. The devices and methods of the present invention can be used in combination electronic sensors, within or external to the device to record pressure, volume, frequency of manual ventilation, delivery pressures, and the like.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for modifying a bag valve mask (BVM) including a bag assembly having a bag connector for detachably mating to a mask connector on a patient mask, said method comprising:
   providing a pressure safety device (PSD) having a bag port and a mask fitting and a flow path from the bag port to the mask fitting; and
   connecting the bag port and the mask fitting of the PSD to the bag connector and the mask connector of the BVM, respectively;
   wherein the PSD is configured to impede breathing gas flow from the BVM to the breathing mask when a pressure or flow rate of the breathing gas entering the bag port of the PSD exceeds a maximum threshold value;
   wherein the PSD comprises a deformable seal having an open position and a closed position, wherein the deformable seal is configured to deform to fully block the flow path in response to the pressure or flow rate exceeding the maximum threshold value.

2. The method of claim 1, wherein the maximum threshold value is a pressure in a range from 9 mmHg to 20 mmHg.

3. The method of claim 1, wherein the maximum threshold value comprises a peak flow in a range from 30 l/min to 70 l/min.

4. The method of claim 1, wherein the PSD further comprises a one-way valve located in the flow path and oriented to divert exhalation flow from the mask fitting.

5. The method of claim 4, wherein the PSD releases exhalation flow from the one-way valve to an exterior of the PSD.

6. A bag valve mask (BVM) assembly comprising:
   a manifold;
   a compression bag attached to deliver a breathing gas to the manifold;
   a breathing mask attached to receive the breathing gas from the manifold; and
   an automatic flow reduction valve located on a flow path in the manifold between the compression bag and the breathing mask, said automatic flow reduction valve being configured to impede flow when a flow rate or a pressure on the compression bag side of the automatic flow reduction valve exceeds a maximum threshold value;

wherein the automatic flow reduction valve comprises a deformable seal having an open position and a closed position wherein the deformable seal is configured to deform to fully block the flow path in response to the pressure or flow rate exceeding the maximum threshold value.

7. The BVM assembly of claim 6, wherein the maximum threshold value is a pressure in a range from 5 mmHg to 20 mmHg.

8. The BVM assembly of claim 6, wherein the maximum threshold value comprises a peak flow rate in a range from 30 l/min to 70 l/min.

9. The BVM assembly of claim 6, wherein the automatic flow reduction valve comprises an umbrella valve including a support plate with flow openings therethrough, wherein the deformable seal is coupled to the support plate, wherein the deformable seal is positioned above the flow openings in the open position and covers the flow openings in the closed position, and wherein a conical periphery is configured to evert to fully seal the openings in response to the pressure or flow rate exceeding the maximum threshold value.

* * * * *